United States Patent [19]

Gillis

[11] 4,411,992

[45] Oct. 25, 1983

[54] PROCESS FOR PREPARING MURINE INTERLEUKIN 2

[75] Inventor: Steven Gillis, Woodinville, Wash.

[73] Assignee: Immunex Corporation, Seattle, Wash.

[21] Appl. No.: 249,906

[22] Filed: Apr. 14, 1981

[51] Int. Cl.$^3$ .................. C12P 21/00; C12P 1/00; C12P 21/02; C12N 5/00; C12N 5/02; C12R 1/91; A61K 37/00

[52] U.S. Cl. .................. 435/68; 435/240; 435/241; 435/948; 435/41; 435/70; 424/177

[58] Field of Search .............. 435/68, 240, 948, 241, 435/41, 70; 424/177

[56] References Cited

PUBLICATIONS

Farrar and Fuller-Bonar, Fed. Proc. 39, 802 (1980).
Gillis, Scheid, Watson, Chem. Abstr. 94:28660 (1981).
Gillis and Watson, J. Exp. Med. 152, 1709 (1980).
Watson et al., Chem. Abstr. 96:33000 (1981).
Yung et al.: J. Immunol. 127, 794 (1981).
Farrar et al., "Biological Relationship of Thymocyte Mitogenic Factor and Factors Enhancing Humoral and Cell-Mediated Immune Responses", 121 *The Journal of Immunology*, 1353 (1978).
Watson et al., "Biochemical and Biological Characterization of Lymphocyte Regulatory Molecules-I. Purification of a Class of Murine Lymphokines", 150 *Journal of Experimental Medicine*, 849 (1979).
Gillis et al., "Biochemical Characterization of Lymphocyte Regulatory Molecules-II. Purification of a Class of Rat and Human Lymphokines", 124 *The Journal of Immunology*, 1954 (1980).
Morgan et al., "Selective *in vitro* Growth of T Lymphocytes from Normal Human Bone Marrow", 193 *Science*, 1007 (1976).
Ruscetti et al., "Functional and Morphological Characterization of Human T Cells Continuously Grown *in vitro*", 119 *The Journal of Immunology*, 131 (1977).
Gillis et al., "Long Term Culture of Tumor Specific Cytotoxic T Cells", 268 *Nature*, 154 (1977).
Gillis et al., "T-Cell Growth Factor: Parameters of Production and a Quantative Microassay for Activity", 120 *The Journal of Immunology*, 2027 (1978).

*Primary Examiner*—Alvin E. Tanenholtz
*Assistant Examiner*—J. Martinell
*Attorney, Agent, or Firm*—Christensen, O'Connor, Johnson & Kindness

[57] ABSTRACT

A process for preparing murine IL-2 from malignant neoplastic cells includes culturing murine leukemia or lymphoma cells in vitro in a protein containing medium supplemented with various additives. An optimum concentration of a T cell mitogen is added to the culture medium to stimulate maximum production of a supernate which contains IL-2. After a period of time, the supernate is collected and purified into more concentrated form. Phorbol myristate acetate may be added to a suboptimum concentration of the T cell mitogen to reduce the quantity of the mitogen required to produce maximum quantities of murine IL-2.

25 Claims, 2 Drawing Figures

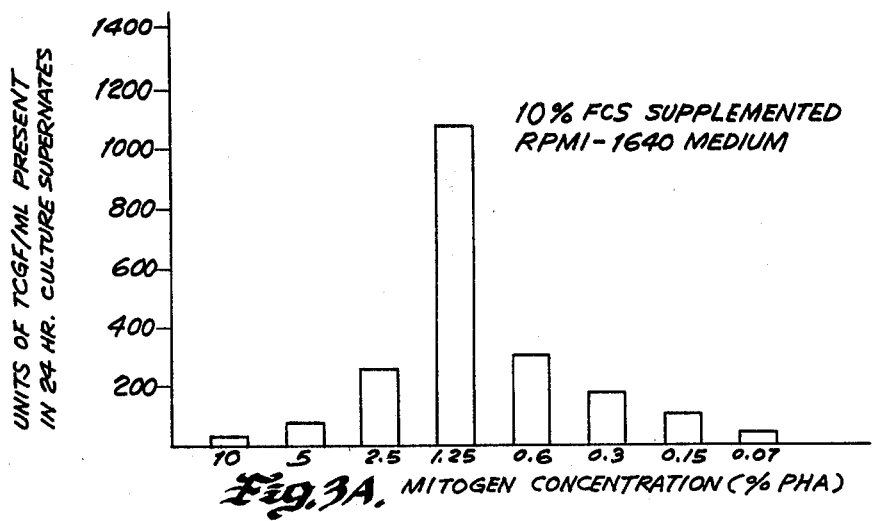
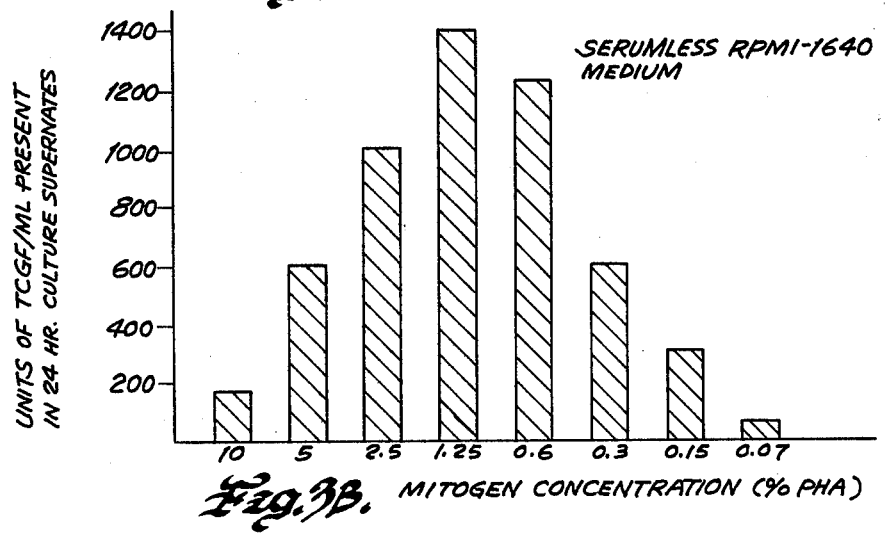

PROCESS FOR PREPARING MURINE INTERLEUKIN 2

DESCRIPTION

Technical Field

The present invention relates to a process for preparing murine interleukin 2 (hereinafter "IL-2"), formerly known in the literature as "T cell growth factor" or "TCGF", and more particularly to a process for producing IL-2 from malignant murine cells.

BACKGROUND ART

IL-2 is a soluble protein which is capable of modulating lymphocyte activation (mitogenesis) and, in the past, has been produced by stimulating mouse, rat or human lymphocyte cells with a mitogen. For instance, Morgan et al. in "Selective in vitro Growth of T Lymphocytes from Normal Human Bone Marrow", 193 Science 1007 (1976) and Ruscetti et al., in "Functional and Morphological Characterization of Human T Cells Continuously Grown in vitro", 119 The Journal of Immunology 131 (1977), both discussed a process for culturing pooled normal human lymphocytes in Roswell Park Memorial Institute (hereafter "RPMI") medium containing autologous serum and the mitogen, phytohemagglutinin (hereafter "PHA").

Gillis and Smith, in "Long Term Culture of Tumor-Specific Cytotoxic T Cells", 268 Nature 154 (1977), reported preparing murine IL-2 by stimulating with the mitogen concanavalin A (hereafter "Con A"), a culture medium composed of normal DBA/2 spleen cells conditioned with RPMI 1640 and fetal calf serum (hereafter "FCS")), and Farrar et al. in "Biological Relationship of Thymocyte Mitogenic Factor and Factors Enhancing Humoral and Cell-Mediated Immune Responses", 121 The Journal of Immunology 1353 (1978), disclosed preparing IL-2 from normal murine spleen cells incubated with Con A in a tissue culute medium containing normal mouse serum (hereafter "NMS").

Gillis et al. reported generating IL-2 from normal murine and rat spleen cells cultured in a medium consisting of RPMI 1640 tissue culture medium supplemented with heat-inactivated FCS, penicillin-G, and gentamycin in a humidified atmosphere of $CO_2$ and air. The murine and rat spleen cells were stimulated by various mitogens including Con A, PHA and pokeweed mitogen (hereafter "PKM"). "Cell Growth Factor: Parameters of Production and a Quantative Microassay for Activity", 120 The Journal of Immunology 2027 (1978).

Gillis et al. in "Biochemical and Biological Characterization of Lymphocyte Regulatory Molecules V. Identification of an Interleukin-2 Producing Human Leukemia T Cell Line", 152 The Journal of Experimental Medicine 1709 (1980), identified the preparation of IL-2 from a human malignant T cell line, specifically malignant leukemic T cells (Jurkat-FHCRC) cultured in RPMI 1640 supplemented with heat-inactivated FCS, N-2-hydroxy-piperazine-XI[1]-2-ethene-sidfonic acid (hereafter "Hepes") buffer, penicillin, streptomycin, $NaHCO_3$ and fresh L-glutamine. The cultures were stimulated with various mitogens including Con A, PHA and PKM.

IL-2 purified from these mouse, rat and human cell lines has been found to retain different types of biological activity, including: (1) marked enhancement of thymocyte mitogenesis, Farrer et al., supra, 121 The Journal of Immunology 1352; (2) promotion of long term in vitro proliferation of antigen specific helper or killer T cell lines, Gillis and Smith, supra, 268 Nature 154, and Watson, "Continuous Proliferation of Murine Antigen Specific Helper T Lymphocytes in Culture", 150 Journal of Experimental Medicine 1510 (1979); (3) induction of cytotoxic T lymphocyte (hereafter "CTL") generation in both alloantigen-stimulated thymocyte and nude spleen cell cultures, Watson et al., "Biochemical and Biological Characterization of Lymphocyte Regulatory Molecules I. Purification of a Class of Murine Lymphokines", 150 Journal of Experimental Medicine 849 (1979), and Gillis et al., "Biochemical and Biological Characterization of Lymphocyte Regulatory Molecules II. Purification of a Class of Rat and Human Lymphokines", 124 The Journal of Immunology 1954 (1980); and (4) promotion of anti-erythrocyte, (Red Blood Cell) plaque-forming cell responses in nude spleen cell cultures stimulated with sheep red blood cells, Watson et al., supra, 150 Journal of Experimental Medicine 849, and Gillis et al, supra, 124 The Journal of Immunology 1954. Accordingly, these identified biological activities of IL-2 in immune response assays indicate that murine IL-2 is useful in the study of immune responses in various diseases, such as immune deficient or neoplastic diseases.

The above cited articles by Gillis & Smith, 268 Nature 154; and Farrar et al., 121 The Journal of Immunology 2027, discuss production of murine IL-2 from lectin stimulated normal spleen cells. However, current production sources and techniques result in very weak concentrations of IL-2. Fractionation of large volumes of conventionally prepared conditioned media containing IL-2 results in only very small quantities of purified murine IL-2. As a consequence, sufficient quantities of concentrated murine IL-2 have not been available for in vivo experiments nor have been available to study the finite molecular character of this lymphocyte regulatory molecule. Accordingly, a principal object of the present invention is to identify cell lines and clones thereof which are potent producers of murine IL-2 and also to ascertain the particular conditions and specific mitogens which foster optimum production of murine IL-2 from such identified cell lines and cell line clones.

DISCLOSURE OF THE INVENTION

The present invention relates to a process for preparing IL-2 from malignant murine cells as set forth by Gillis et al. in "Biochemical and Biological Characterization of Lymphocyte Regulatory Molecules III. The Isolation and Phenotypic Characterization of Interleukin 2-Producing T Cell Lymphomas", 125 The Journal of Immunology 2570 (1980). The process includes culturing malignant cells, such as murine leukemia and lymphoma cells in vitro in a protein containing medium supplemented with various additives. The culture is stimulated by a T cell mitogen thereby producing a supernate which contains IL-2. After a period of time, the supernate is collected and processed to purify the IL-2.

The process also includes cloning such tomor cell lines by suspending single cell samples of malignant murine cell lines found to produce IL-2 in vitro in a culture medium. After single cell cultures have grown to appropriate densities, the medium is stimulated with a T cell mitogen to produce an IL-2 containing supernate. As with the parent cell line, cloned cell supernates are processed to concentrate the IL-2 contained therein.

The above process has been used in conjunction with a particular murine radiation-induced splenic lymphoma cell line from the B10.BR mouse, designated as LBRM-33. Use of the cells in a culture medium composed of RPMI 1640 medium together with certain additives and a plant mitogen, such as PHA or Con A has been found to produce between 1000 and 5000 times more murine IL-2 per milliliter than previously generated by lectin stimulation of rat or mouse splenocytes cultured at identical concentrations. Applicant has established that the initial cell concentration of the particular T leukemic or T lymphoma cell used affects the volume of IL-2 production. The concentration of the specific plant mitogen used also influences IL-2 production.

The primary component of the culture medium may consist of commercially available media, such as RPMI medium, Click's medium, and Dulbecco Modified Eagle Medium (hereafter "DMEM"). Additives which may be individually or in combination added to the culture medium include penicillin, streptomycin, fresh glutamine, Hepes buffer, $NaHCO_3$, 2-mercaptoethanol, and FCS.

An unsaturated fatty acid phorbol ester may be added to the culture medium to in part replace the need for a T cell mitogen to produce IL-2. For instance, phorbol myristate acetate (hereafter "PMA") added to a culture medium containing LBRM-33 cells stimulated by a 1/10 optimum concentration of PHA or Con A has been found to boost IL-2 production back up to the level produced when optimum concentrations of these two mitogens alone are used. However, adding various concentrations of PMA to cultures stimulated with optimum concentrations of PHA or Con A did not result in a boost of IL-2 production.

BRIEF DESCRIPTION OF THE DRAWINGS

The details of typical embodiments of the present invention are described in connection with the accompanying drawings in which:

FIG. 3A illustrates the quantity of IL-2 (TCGF) produced when various concentrations of the T-cell mitogen PHA are used to culture a concentration of $1 \times 10^6$ LBRM-33 cells for 24 hours in RPMI medium supplemented with 10% by volume heat-inactivated FCS;

FIG. 3B is similar to FIG. 3A, but without any FCS added to the RPMI medium.

BEST MODE OF THE INVENTION

Outline of Process

Figure 1A:
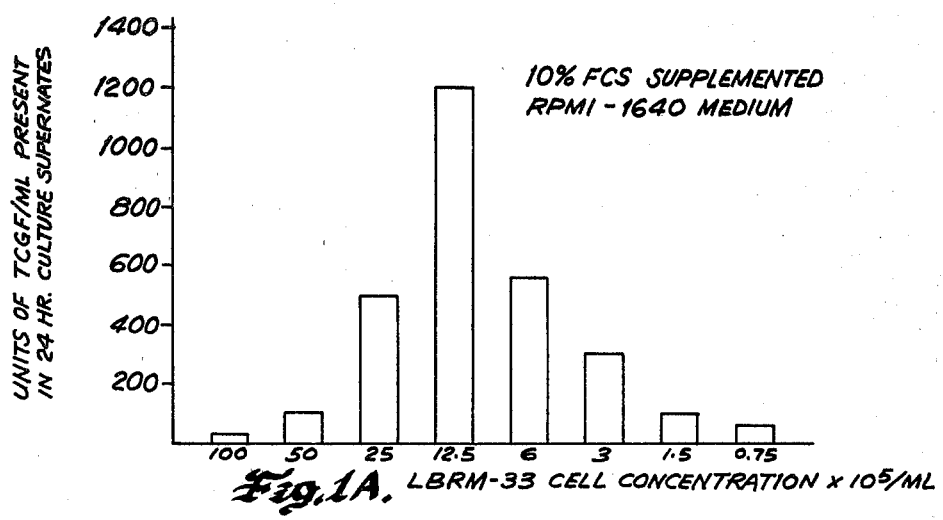
FIG. 1A is a graph illustrating the quantities of IL-2 -produced per milliliter of culture supernate when various initial cell concentrations of the LBRM-33 cell line are cultured for 24 hours in RPMI medium supplemented with 10% by volume quantity of heat-inactivated FCS.

In accordance with the present invention, murine malignant neoplastic cells in the form of leukemia and lymphoma cells are cultured in vitro in a protein containing medium supplemented with various additives. T cell mitogen is added to the culture medium to stimulate the production of a supernate which contains IL-2. After a period of time, the supernate is collected and processed to purify the IL-2 into a more concentrated form. Also, cell lines found to be significant producers of IL-2 are cloned and then cultured in a protein medium and stimulated with a T cell mitogen to generate an IL-2 containing supernate. As another part of the present invention, phorbol esters are used as a co-stimulant with a suboptimum concentration of T cell mitogen to reduce the amount of mitogen required to produce IL-2. The process of the present invention has been described by Gillis et al. in "Biochemical and Biological Characterization of Lymphocyte Regulatory Molecules III. The Isolation and Phenotypic Characterization of Interleukin-2 Producing T Cell Lymphomas", 125 *The Journal of Immunology* 2570 (1980).

Applicant has used the above process in conjunction with various leukemic T cell lines and also in conjunction with various T lymphoma cell lines wherein the cell lines were produced by either spontaneous occurrence, viral infection, chemical carcinogen or radiation. Cell lines were collected from tissue culture sources at the Memorial Sloan-Kettering Cancer Center and the Univ. of California at Irvine. Of the various murine T cell leukemia and lymphoma lines tested, as set forth in Table I below, one particular cell line, a radiation-induced splenic lymphoma from the B10.BR mouse, designated as LBRM-33, was found to produce several hundred times the amount of IL-2 per milliliter than had been previously generated by an equivalent number of mitogen-stimulated rat or mouse splenocytes. Another cell line from the C57BL/6 mouse spleen cells, specified as RBL-3, also produced minor quantities of IL-2 per milliliter.

TABLE I

Screening of murine leukemia and lymphoma cells for IL-2 production

| Cell Line | Strain of Origin | Inducing Agent | IL-2 Activity Present in 48-hr Supernatant after Activation with | | | |
|---|---|---|---|---|---|---|
| | | | Medium[1] | Con A[2] U/ml | PHA[3] | LPS[4] |
| T Cell Tumors | | | | | | |
| RBL-5 | C57BL/6 | RLV | 0.0 | 0.0 | 0.0 | 0.0 |
| EL-4 | C57BL/6 | Benzapyrene | 0.0 | 0.0 | 0.0 | 0.0 |
| CEL 41 | C57BL/6 | Subclone of El-4 | 0.0 | 0.0 | 0.0 | 0.0 |
| CEL 43 | C57BL/6 | Subclone of EL-4 | 0.0 | 0.0 | 0.0 | 0.0 |
| CEL 49 | C57BL/6 | Subclone of EL-4 | 0.0 | 0.0 | 0.0 | 0.0 |
| L51784 | B10.129 5.M | Spontaneous | 0.0 | 0.0 | 0.0 | 0.0 |
| S49 | BALB/c | Mineral oil | 0.0 | 0.0 | NT[5] | NT |
| BW5147 | AKR | Spontaneous | 0.0 | 0.0 | NT | NT |

TABLE I-continued
Screening of murine leukemia and lymphoma cells for IL-2 production

| | | | \multicolumn{4}{c}{IL-2 Activity Present in 48-hr Supernatant after Activation with} | | | |
|---|---|---|---|---|---|---|
| Cell Line | Strain of Origin | Inducing Agent | Medium[1] | Con A[2] U/ml | PHA[3] | LPS[4] |
| RDM4 | AKR/I | Spontaneous | 0.0 | 0.0 | 0.0 | 0.0 |
| RBL-3 | C57BL/6 | RLV | 0.0 | 0.0 | 0.08 | 0.0 |
| RBL-31 | C57BL/6 | Subclone of RBL-3 | 0.06 | 0.56 | 0.31 | 0.0 |
| RBL-31C | C57BL/6 | Subclone of RBL-3 | 0.11 | 0.64 | 0.37 | 0.0 |
| RBL-3M | C57BL/6 | Subclone of RBL-3 | 0.0 | 0.0 | 0.0 | 0.0 |
| YAC-1 | A/SN | Mo-MuLV | 0.0 | 0.0 | 0.0 | 0.0 |
| TIMI | C57BL/6 | Radiation | 0.0 | 0.0 | NT | NT |
| R1.1 | BALB/c | Radiation | 0.0 | 0.0 | NT | NT |
| RAD-A1 | A | Radiation | 0.0 | 0.0 | 0.0 | 0.0 |
| ASL-1 | A | Spontaneous | 0.0 | 0.0 | 0.0 | 0.0 |
| RL$\sigma$-1 | BALB/c | Radiation | 0.0 | 0.0 | 0.0 | 0.0 |
| HRST 34 | hr/hr | Spontaneous | 0.0 | 0.0 | 0.0 | 0.0 |
| LBRM-33 | B10.Br | Radiation | 0.0 | 26.0 | 517.0 | 0.0 |
| 1A5 | B10.Br | Subclone of LBRM-33 | 0.0 | 0.0 | 0.0 | 0.0 |
| 4C1 | B10.Br | Subclone of LBRM-33 | 0.0 | 0.15 | 4.3 | 0.0 |
| 5A4 | B10.Br | Subclone of LBRM-33 | 0.0 | 35.0 | 866.0 | 0.0 |
| 4A2 | B10.Br | Subclone of LBRM-33 | 0.0 | 42.0 | 1163.0 | 0.0 |
| 6B1 | B10.Br | Subclone of LBRM-33 | 0.0 | 32.0 | 927.0 | 0.0 |
| Normal mouse splenocytes ($10^6$ cells/ml) | | | 0.0 | 0.32 | 0.13 | 0.0 |
| Normal mouse splenocytes ($10^7$ cells/ml) | | | 0.0 | 1.13 | 0.87 | 0.0 |
| Normal rat splenocytes ($10^6$ cells/ml) | | | 0.0 | 1.0 | 0.86 | 0.0 |
| Normal rat splenocytes ($10^7$ cells/ml) | | | 0.0 | 13.6 | 7.85 | 0.0 |

[1] Click's 10% FCS.
[2] 25 μg/ml.
[3] 1% PHA-M by volume.
[4] 100 μg/ml.
[5] NT. not tested.

Figure 1B:
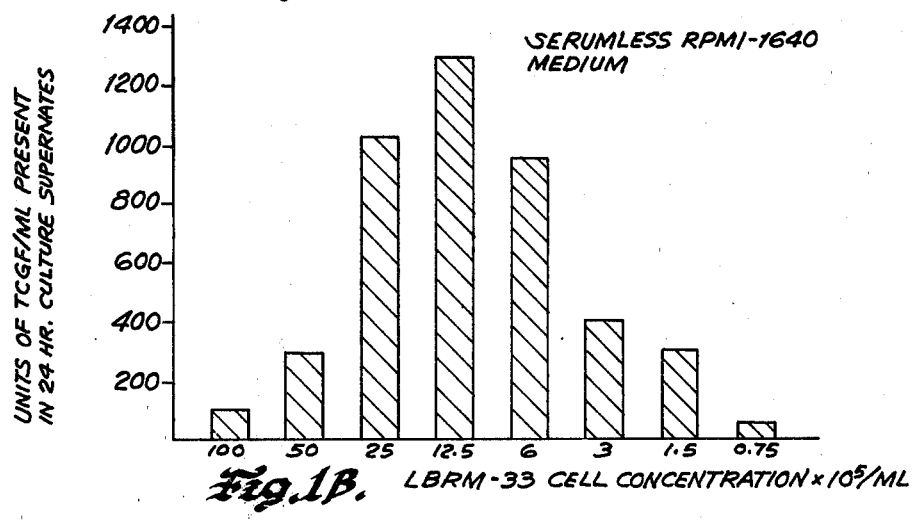
FIG. 1B is graph similar to FIG. 1A, but without any FCS added to the RPMI medium.

Applicant has found that the initial cell density of a particular malignant cell line used in the culture process affects the quantity of IL-2 produced by mitogen stimulation per number of initial cells. For instance, as set forth in FIG. 1A and 1B, in the LBRM-33 cell line, when beginning with a concentration of $7.5 \times 10^4$ cells per milliliter, approximately 50 units of IL-2 per milliliter are produced after 24 hours when the cells are cultured in RPMI medium and stimulated with a one percent by volume concentration of PHA either with (FIG. 1A) or without (FIG. 1B) a 10% by volume quantity of heat inactivated FCS. When the initial cell concentration is increased to approximately $1.25 \times 10^6$ cells per milliliter, a maximum of approximately 1300 units of IL-2 per milliliter without FCS (FIG. 1B) and 1200 units of IL-2 per milliliter with FCS (FIG. 1A) are produced. If, however, the concentration of LBRM cells is further increased to, for instance, $1.0 \times 10^7$ cells per milliliter, the production of IL-2 drops back down to approximately 100 units per milliliter without FCS (FIG. 1B) and 25 units per milliliter with FCS (FIG. 1A). Thus, if LBRM cells are used, the initial density of the cells preferably should be in the range of about $6 \times 10^5$ cells per milliliter to $3 \times 10^6$ cells per milliliter, with an ideal concentration of approximately $1 \times 10^6$ cells per milliliter.

Through phenotypic characterization, the LBRM-33 cell line, and its subclones which are listed in Table I above, have found to express Thy 1, Ly 1, Ly 2, Ly 3 and Ly 5 differentiation antigens. The LBRM-33 cells and its clones were also found to display Qa2.3, Qa3 and Qa T4 cell-surface differentiation antigens.

The murine malignant cell lines, and particularly the LBRM-33 lymphoma cells, may be grown in various appropriate cell culturing media which have been previously found to foster growth of lymphocytes. These culture media include RPMI-1640, Click's medium and DMEM. These culture media may be supplemented with various individual additives or combinations of additives, including FCS which has been heat-inactivated by, for example, applying heat at 56° C. for 30 minutes. The quantity of FCS added may be from 2 to 10 percent of the total culture volume. Another additive is penicillin in a concentration range of approximately 25 to 250 units per milliliter, and preferably approximately 50 units per milliliter. Streptomycin may also be utilized as an additive in a preferred concentration range of from 25 to 250 micrograms per milliliter, and ideally approximately 50 micrograms per milliliter. Further additives include: (i) fresh L-glutamine in a preferred concentration range of approximately 150 to 500 micrograms per milliliter, with an ideal concentration of approximately 300 micrograms per milliliter; (ii) Hepes' buffer in a preferred concentration of from 10 to 35 mM, and ideally approximately 25 mM; and (iii) 2-mercaptoethanol in a preferred amount of $1 \times 10^{-5}$ to $5 \times 10^{-5}$ molar, and ideally approximately $2.5 \times 10^{-5}$ molar. NaHCO$_3$ in a concentration range of 1 to 30 millimolar and ideally about 16 millimolar may be used in the culture media.

Figure 2:
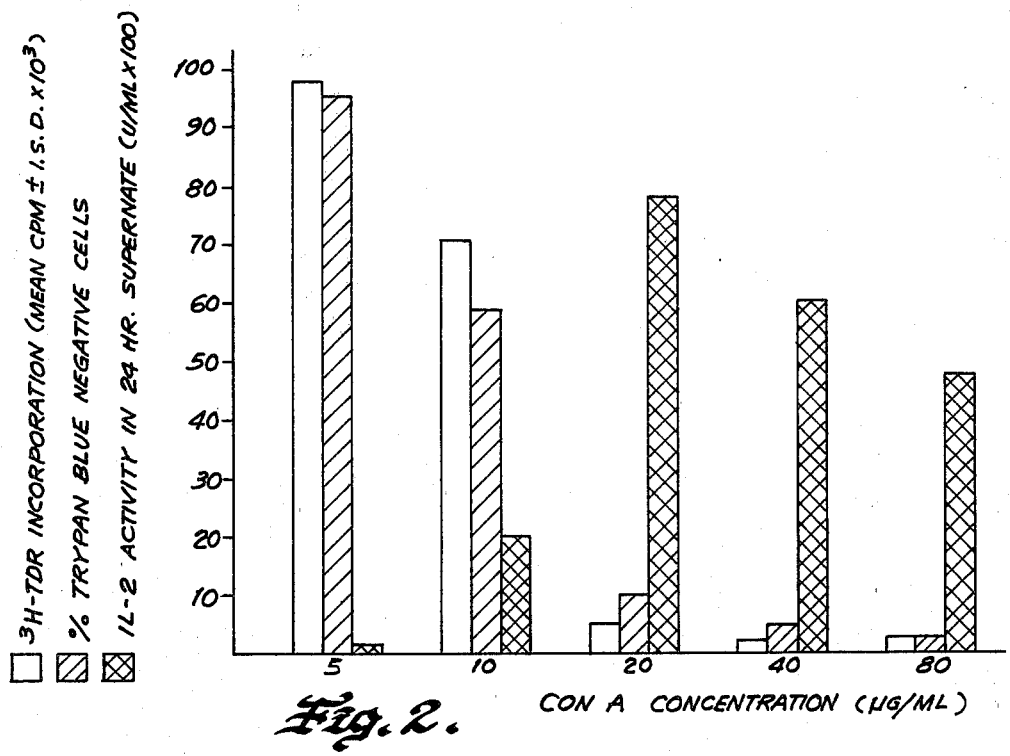
FIG. 2 illustrates the relationship of IL2 production and LBRM-33 cell viability when different concentrations of Con A are used to culture a concentration of $1 \times 10^6$ LBRM-33 cells per milliliter in RPMI 1640 medium.

In the IL-2 production process of the present invention, several different stimulating mitogens may be utilized. These mitogens include different plant glycoproteins such as Con A, PHA, and PKM. Applicant has found that the specific concentration of the particular mitogen used affects the quantity of IL-2 produced. This is illustrated in FIG. 2 which depicts the relationship of IL-2 production and LBRM-33 cell viability, for different concentrations of Con A are used to stimulate LBRM-33 cells at a concentration of $1 \times 10^6$ cells per milliliter RPMI 1640 medium. For instance, if a concentration of 10.0 micrograms per milliliter of Con A is used, in approximately 24 hours about 200 units per milliliter of IL-2 are produced. When 20 micrograms per milliliter of Con A are employed, approximately 800 units of IL-2 per milliliter are obtained. However, if the concentration of Con A is further increased to 80 micrograms per milliliter, only 500 units per milliliter of IL-2 results. Accordingly, when Con A is used as a mitogenic stimulant for LBRM-33 cells at a concentration of $1 \times 10^6$ cells per milliliter, an optimum concentration of Con A is from approximately 20 to 50 micrograms per milliliter. It is to be understood that if different concentrations of LBRM-33 cells are employed, or if another cell line is used, the concentration of Con A may have to be adjusted to obtain maximum IL-2 production.

As indicated in FIGS. 3A and 3B above, the particular concentration of PHA mitogen added to a LBRM-33 cell culture also affects the quantities of IL-2 produced per initial cell concentration of the LBRM cells. FIG. 3A illustrates the quantity of IL2 (TCGF) produced for different concentrations of PHA when a cell concentration of $1 \times 10^6$ LBRM-33 cells aare cultured for 24 hours in RPMI medium supplemented with 10% by volume heat-inactivated FCS. FIG. 3B shows IL-2 production for LBRM-33 cells cultured in RPMI medium, but without any FCS. As shown in FIG. 3B, if unsupplemented RPMI 1640 medium is used a 0.15% concentration of PHA has been found to result in IL-2 activity in the amount of approximately 300 units per milliliter. However, if the PHA concentration is increased to approximately 1.25%, a maximum quantity of about 1400 units per milliliter of IL-2 is produced. Increasing the PHA concentration to above this level has been found negatively to affect IL-2 production. For example, when the PHA concentration is increased to 10% by volume, the IL-2 activity drops down to approximately 180 units per milliliter. As shown in FIG. 3A, similar results occur if the RPMI 1640 medium is supplemented with 10% by volume heat-inactivated FCS. Accordingly, for optimum stimulation of LBRM-33 cells at a concentration of approximately $1 \times 10^6$ cells per milliliter, a PHA mitogen concentration in the range of 0.5% to 2% by volume should be used, with the ideal concentration being approximately 1% by volume.

The quantity of IL-2 produced by stimulating malignant murine cells with a plant mitogen varies with time. For instance, when $10^6$ cells are cultured in RPMI-1640 supplemented with FCS and stimulated with a 1% by volume concentration of PHA, IL-2 activity first appears in the culture at about five to seven hours after PHA stimulation. Initial IL-2 activity occurs within this five to seven hour time period even if FCS is not added to the culture medium. Whether or not FCS is used, peak levels of IL-2 are reached at approximately sixteen to twenty-four hours after stimulation by PHA. In the subsequent twenty-four hour period, the quantity of IL-2 present diminishes slightly. Thus, the optimal culture duration for producing IL-2 with LBRM-33 cells in a RPMI-1640 medium activated with 1% by volume PHA is approximately from sixteen to forty-eight hours.

The above-described process for producing IL-2 from murine malignant cell lines, such as LRBM-33 lymphoma cells, may be carried out in various environmental conditions. Preferably, however, the LRBM-33 culture should be maintained at a temperature range of approximately 35° to 38° C. and in a humidified atmosphere of approximately 5 to 10% carbon dioxide in air. Also, ideally the pH of the culture medium should be kept in slightly alkaline condition, in the range of approximately pH 7.0 to 7.4.

The malignant cell lines may be seeded in different types of containers including flat-bottom microplate wells and in various sizes such as in 100-microliter aliquots. Tissue culture flasks, such as flasks No. 3013 or 3024 from Falcon Labware, Div. Becton, Dickinson and Co. also may be used. Alternatively, a roller bottle, such as bottle No. 3027 also from Falcon Labware, may be used as a container for the culture. The present invention also includes identifying potent cell line sources of IL-2 by cloning cell lines known to produce significant quantities of IL-2. Thereafter, the cloned cell lines are cultured in a medium which may be supplemented with various additives and stimulated with a plant mitogen in much the same manner in which IL-2 is produced frm LBRM-33 lymphoma cells, as outlined above. Cloning is accomplished by a limiting dilution procedure wherein cells from selected cell lines, such as LBRM-33 and RBL-3 are cultured in flat-bottom microplate wells. The cells are seeded in 200 microliter volumes of RPMI-1640 supplemented with FCS at a cell density of 1 cell per milliliter. After ten days, the microplate wells which house viable cell growth are harvested and then subcultured in tissue flasks containing a medium composed of RPMI-1640 supplemented with FCS. A plant mitogen, such as PHA or Con A is used to stimulate the viable cell IL-2 production. Use of this procedure to subclone RBL-3 and LBRM-33 cells has been found to result in a 50 to 70% plating efficiency. Once the subcloned cultures have reached a density of approximately $10^6$ cells per milliliter, cultures are harvested and tested for IL-2 production.

As set forth in Table I above, from a parent LRBM-33 cell line, subclones labeled as 5A4, 4A2 and 6B1 were found to produce even greater quantities of IL-2 than generated by the parent line. The same was found to be true for two subclones, designated as RBL-31 and RBL-31C produced from the parent RBL-3 cell line. In control cultures in which the subcloned cells were cultured without stimulation by a plant mitogen, no IL-2 was produced.

Production of IL-2 from murine malignant cell lines may be enhanced by adding phorbol esters such as PMA to one of the plant mitogens listed above. For instance, it has been found that when LRBM-33 cells in an optimum concentration of $10^6$ cells per milliliter are cultured in RPMI-1640 supplemented with 10% by volume FCS, if a sub-optimum concentration of 0.1% PHA is used as a stimulant, after twenty-four hours approximately 26 units of IL-2 are produced. However, if this sub-optimum concentration of PHA is supplemented with from 10 to 30 nanograms per milliliter of PMA, IL-2 production is restored back up to approximately 900 units per milliliter which is about equal to the activity level of IL-2 produced when an optimum concentration of 1% PHA is utilized alone (see Table II below). Thus, adding PMA to the malignant cell culture significantly reduces the concentration of mitogen needed to produce a given level of IL-2. This has the advantage of requiring less effort to remove the mitogen contamination during purification of the IL-2.

Enhanced IL-2 production by PMA, however, does not occur when an optimum concentration of the mitogen PHA is used. As set forth in Table II below, if PMA at a concentration of from 10 to 50 nanograms per milliliter is added to an optimum concentration of 1.0% by volume PHA, the IL-2 activity level remains substantially the same as when a 1% concentration of PHA is used alone.

Very similar results, as indicated in Table II, occur when Con A is used as a culture stimulant. Also, applicant has found that the use of PMA alone in concentrations of 10 to 50 nanograms per milliliter without any mitogen stimulation results in little IL-2 production. Accordingly, it appears that although IL-2 production may be boosted by addition of PMA to sub-optimum concentrations of plant mitogens, PMA cannot serve as a substitute for an appropriate plant mitogen.

TABLE II

Effect of phorbol myristate acetate (PMA) on LBRM-33 IL-2 Production

| LBRM Culture Stimulants | | | % Viable LBRM-33 Cells Remaining after 24-h Culture | IL-2 Activity Presents in 24-h Culture Supernatant U/ml |
|---|---|---|---|---|
| PHA | CON A | PMA | | |
| —[1] | — | — | 100 | 0.0 |
| — | — | 10 ng/ml | 95 | 0.0 |
| — | — | 30 ng/ml | 98 | 0.0 |
| — | — | 50 ng/ml | 100 | 0.0 |
| — | 20 µg/ml | — | 4 | 783.0 |
| — | 20 µg/ml | 10 ng/ml | 3 | 815.0 |
| — | 20 µg/ml | 30 ng/ml | 3 | 762.0 |
| — | 20 µg/ml | 50 ng/ml | 6 | 801.0 |
| — | 2 µg/ml | — | 87 | 16.0 |
| — | 2 µg/ml | ng/ml | 13 | 673.0 |
| — | 2 µg/ml | 30 ng/ml | 4 | 712.0 |
| — | 2 µg/ml | 50 ng/ml | 3 | 706.0 |
| 1% | — | — | 2 | 864.0 |
| 1% | — | 10 ng/ml | 1 | 912.0 |
| 1% | — | 30 ng/ml | 6 | 831.0 |
| 1% | — | 50 ng/ml | 5 | 869.0 |
| 0.1% | — | — | 91 | 26.0 |
| 0.1% | — | 10 ng/ml | 6 | 935.0 |
| 0.1% | — | 30 ng/ml | 6 | 932.0 |
| 0.1% | — | 50 ng/ml | 3 | 869.0 |

[1]—, Absent from culture

IL-2 may be concentrated or purified from culture supernates by various procedures, such as salt precipitation, ion exchange chromatography, gel chromatography, preparative iso-electric focusing (hereafter IEF), and/or gel electrophoresis.

An example of purification of IL-2 utilizing ion exchange chromatography, gel filtration and IEF is set forth below in Example 2.

Microassay of IL-2

The activity levels of IL-2 produced by the mitogen stimulation of various malignant murine cell lines, to ascertain what combinations of cell lines and mitogens produce significant quantities of IL-2, may be tested by using the microassay procedure discussed by Gillis et al. in "T-Cell Growth Factor: Parameters of Production and a Quantative Microassay for Activity", 120 *The Journal of Immunology* 2027 (1978). The assay monitors the IL-2 dependent cellular proliferation of a mouse cytotoxic T cell line (hereafter "CTLL"). Once potential combinations of cell lines and mitogens are identified, such as LBRM-33 cells stimulated by PHA, the microassay technique is then employed to determine optimum culture conditions for IL-2 production, such as the optimum initial cell concentration of LBRM-33, optimum mitogen doses, and harvest times, as discussed above.

Briefly, the microassay procedure includes seeding approximately 3000 CTLL cells in 200 microliter volumes in a $\log_2$ dilution series of potential IL-2-containing samples. The mixture is cultured for twenty-four hours at 37° C. in a humidified atmosphere of 5% carbon dioxide in air. Thereafter, the cultures are pulsed for approximately four hours with 0.5 microcurie of tritiated thymidine ($[^3H]$Tdr; 20 mCi/mM sp act) after which time the cultures are harvested onto glass fiber filter strips, for instance with the aid of a multiple automated sample harvester. $[^3H]$Tdr incorporation is then measured by liquid scintillation counting. By this procedure, only the CTLL cells cultures in the presence of IL-2 were found to incorporate $[^3H]$Tdr in a dose-dependent manner. CTLL cells cultured in the absence of IL-2 incorporated only scintillant control levels of $[^3H]$Tdr and were more than 95% trypan-blue positive after twenty-four hours of IL-2 deprivation, indicating that such cells were dead. Units of IL-2 activity were determined by probit analysis of $[^3H]$Tdr incorporation data, as described above, A 1 unit/ml standard has been defined as the amount of IL-2 activity present in forty-eight hour tissue culture medium conditioned by Con A (5 microgram/ml) stimulation of an initial concentration of $10^6$ cells per milliliter of normal rat spleen cells. An assay of 1 unit/ml standard routinely stimulated approximately 10,000 cpm of CTLL $[^3H]$Tdr incorporation at a dilution of 1:2. The results of the microassay of the supernates produced by various murine cell lines stimulated by different mitogens is set forth above in Table I.

Biochemical and biological characterization of murine IL-2

To determine the biochemical and biological characterization of murine LBRM-33 cell derived IL-2, the IL-2 was concentrated by ammonium sulfate precipitation. Fractionation of precipitated IL-2 by Sephadex G-100 column chromatography (as set forth in Example 2), revealed that Il-2 molecules in a size range of approximately 30,000 daltons were eluted. The IL-2 as eluted from the column was pooled and examined by diethyl amino ethyl (hereafter "DEAE") cellulose ion exchange chromotography. Under these conditions LBRM-33 cell produced IL-2 could be sequentially bound and eluted from DEAE cellulose in fractions containing 185 mM NaCl. When pooled DEAE fractionated Il-2 was subjected to preparative IEF, IL-2 activity was found to be centered around two major peaks of activity, with isoelectric values of approximately pH 4.5 and 5.0. The molecular size and the isoelectric values of the IL-2 produced from malignant LBRM-33 cells were identical to the molecular size and isoelectric values previously reported from IL-2 produced from normal mouse spleen cells. Watson et al, supra, 150 *The Journal of Experimental Medicine* 849.

The LBRM-33 dervied IL-2 was also determined to to a proteinaceous substance. This was ascertained by reducing IL-2 with 0.75 moles of 2-mercaptoethanol. It was observed that after such reduction the IL-2 remained stable. Also, the LBRM-33 generated IL-2 was found to be stable after treatment with a denaturing agent, such as urea in 2 M and 4 M concentrations. It was further observed that when the IL-2 was treated with proteolytic enzymes, such as trypsin, subtilisin, chymotrypsin and leucine aminopeptidase, it lost its activity, which is consistent with the conclusion that it is a proteinaceous substance.

Further, as with IL-2 produced with normal murine spleen cells, the activity of LBRM-33 produced IL-2 was found to be stable over a wide range of pH, from approximately pH 2.2 to 8.0. Also, the IL-2 activity was stable after incubation at 37° C. for twelve hours and 56° C. for one hour.

Examples 1A, 1B and 1C

Cell line samples of particular murine leukemic T-cells, LBRM-33, in a concentration of $1 \times 10^6$ cells per milliliter were cultured in 200 microliter flatbottom microplate wells (3596; Costar, Inc., Data Packaging, Cambridge, Mass.), in RPMI 1640 medium. The medium was supplemented with 10% by volume heat-inactivated (56 degrees centigrade for 30 minutes) FCS, 25 millimoles of Hepes buffer, 50 units per milliliter of penicillin, $2.5 \times 10^{-5}$ M 2-mercaptoethanol, 50 micrograms per milliliter of streptomycin, and 300 micrograms per milliliter of fresh L-glutamine. The size of each culture, including the cell line sample, medium and supplements totaled 100 microliters. The microwell cultures were then stimulated by adding 100 microliters of: (Example 1A) Con A in a concentration of 25 micrograms per milliliter (Miles Biochemicals, Inc., Elkhart, Indiana); (Example 1B) PHA at a concentration of 2% by volume (PHA-M, Grand Island Biological Co., Grand Island, NY); and (Example 1C) escherichia coli lipopoly saccharide (hereafter "LPS") in a concentration of 100 micrograms per milliliter (Difco Inc.). The cultures were all maintained at approximately 37° C. in a humidified atmosphere at 5% carbon dioxide in air.

After twenty-four hours, the supernate samples from the cultures were pooled and assayed for IL-2 activity using the microassay procedure as discussed above. The assay determined that IL-2 activity present in the twenty-four hour supernate included approximately 26.0 units per milliliter for the culture activated with Con A and 517.0 units per milliliter for the culture activated by PHA. No IL-2 was produced in the culture stimulated with LPS.

Example 2

LBRM-33 cells at a cell density of $1 \times 10^6$ cells per milliliter were suspended in a tissue culture flask (No. 3024 from Falcon Labware, Div. Becton, Dickinson & Co., Oxnard, CA) in a humidified atmosphere of 5% carbon dioxide in air. RPMI-1640 was used as a medium. This medium was supplemented with 50 units per milliliter of penicillin, 50 micrograms per milliliter of streptomycin, 300 micrograms per milliliter of fresh glutamine, 25 millimolar of Hepes buffer, 16 millimolar of $NaHCO_3$ and $5 \times 10^{-5}$ molar 2-mercaptoethanol. PHA (PHA-M Gibco) in a concentration of 1% by volume was used as a stimulant. After twenty-four hours of culturing, the supernate was centrifuged at 300 xg for 20 minutes. IL-2 in a concentration of 1180 units per milliliter was produced.

The IL-2 produced was purified by the following procedure.

Ammonium sulfate precipitation 980 milliliters of cell-free supernate were filtered through 0.45 micron filter to remove debris. Thereafter, ammonium sulfate was added at 4° C. to produce an 85% saturated solution. The supernate and ammonium sulfate were stirred slowly for 12 hours at 4° C. Thereafter, the mixture was centrifuged at 10,000 xg for 20 minutes. The precipitate obtained was then dissolved in 50 milliliters of 0.05 molar NaCl buffered with 25 mM Hepes at pH 7.2 (hereafter "0.05 molar NaCl Hepes"). This solution was dialysed against the same buffer for forty-eight hours with two changes of dialysing solution.

DEAE-S Sepharose Ion-exchange Chromatography

The supernate as concentrated by the above ammonium sulphate precipitation procedure was dialysed against 0.05 molar NaCl-Hepes buffer (pH 7.2) and then applied onto a DEAE cellulose column (30 centimeters), which was previously equilibrated with 0.05 molar NaCL Hepes buffer. IL-2 was eluted by a 250 milliliter linear gradient of NaCl solution in concentrations of 0.05 to 0.5 moles. IL-2 activity was detected in the fractions which were eluted by NaCl at about 0.18 molar NaCl-Hepes. The IL-2 containing fractions were then pooled and dialysed against 0.9% NaCl-Hepes.

Gel Filtration

The concentrate obtained by the anion exchange chromatography procedure was applied onto a column of AcA54 (LKB Produkter, Sweden) (2×90 centimeters) and eluted with sterile 0.9% NaCl-Hepes buffer. Fractions with IL-2 activity were eluted from AcA54 columns with an apparent molecular weight of 30,000–40,000 daltons. The gel filtration columns were calibrated with the following molecular weight markers: Bovine serum albumin (68,000 daltons); oval bumin (44,000 daltons); and cytochrome C (12,500 daltons).

Gel Electrophoresis

The dialysed IL-2 activity as concentrated by the above gel filtration process was diluted to 100 milliliters with a solution composed of 1% by weight glycine, 0.1% by volume aspartic acid and 2% by volume ampholytes (PH3-10, LKB Produkter, Sweden). Thereafter 4 grams of Ultradex (LKB Produkter, Sweden) was added to the mixture to form a gel suspension which was then spread on a gel tray. The gel tray was placed on a cooling tray and the gel suspension electrophoresed for approximately twenty-four hours under a constant current of 7 milliamps and an increasing voltage of from 100 to 1000 volts. IL-2 activity of the electrophoresed gel was found to be separated into two major peaks, having isoelectric values of approximately pH 4.5 and 5.0. The IL-2 recovered after all of the above steps was microassayed using the above-described assay procedure through which it was determined that the specific activity of the IL-2 had increased to approximately 400–500 times over that of the culture supernate.

Examples 3A, 3B and 3C

LBRM-33 cells were subcloned by a limiting dilution procedure in flat-bottom microplate wells. Individual LBRM-33 cells were seeded in 200 microliter volumes of RPMI-1640 supplemented with FCS. After 10 days of culture, the microplate wells were screened for viable cell growth. Positive wells were harvested and subcultured in 25 centimeter tissue culture flasks (3013, Falcon Plastics, Oxnard, CA) in RPMI-1640 supplemented with FCS. After the subcultures grew to a density of approximately $10^6$ cells per milliliter, they were harvested and resuspended in RPMI-1640 medium supplemented with 10% by volume heat-inactivated FCS, $2.5 \times 10^{-5}$ M 2-mercaptoethanol, 25 millimolar Hepes buffer, 50 units per milliliter penicillin, 50 micrograms per milliliter streptomycin, and 300 micrograms per milliliter fresh L-Glutamine. These clonal subcultures were then stimulated by adding 100 microliters of: (Example 3A) Con A in a concentration of 25 micrograms per milliliter (Miles Biochemicals, Inc., Elkhart, Ind.); (Example 3B) PHA in a concentration of 1% by volume (PHA-M, Grand island Biological Company, Frand Island, NY); and, (Example 3C) LPS in a concentration of 100 micrograms per milliliter (Difco, Inc.). The cultures were all maintained at approximately 37° C. in a humidified atmosphere of 5% carbon dioxide in air. After twenty-four hours, the supernate samples from the clonal subcultures were assayed for IL-2 activity using the microassay procedure as described above. The assay determined that IL-2 activity present in the twenty-four hour supernate included approximately 42.0 units per milliliter for the subclone culture activated with Con A and 1163.0 units per milliliter from the subclone cluture activated by PHA. No IL-2 was produced in the subclone culture stimulated with LPS.

As will be apparent to those skilled in the art to which the invention is addressed, the present invention may be carried out by using murine cell lines and cell lines cloned therefrom, culture media, culture media additives and mitogen stimulants other than those specifically disclosed above, without departing from the spirit or essential characteristics of the invention. The particular processes described above are therefore to be considered in all respects as illustrative and not restrictive, i.e. the scope of the present invention is set forth in the appended claims rather than being limited to the examples of the IL-2 producing processes as set forth in the foregoing description.

What is claimed is:

1. A process for the production of IL-2 from a murine malignant T-cell line, comprising culturing malignant murine T-cells in a culture medium containing a T-cell mitogen, and recovering the IL-2 from the culture medium.

2. The process of claim 1, wherein said malignant murine T-cells are T leukemic cells or T lymphoma cells.

3. The process of claim 2, wherein said T lymphoma cells are from the LBRM-33 lymphoma murine T-cell line.

4. The process of claim 2 or 3, wherein the initial T leukemic or T lymphoma cell concentration is in the range of about $6 \times 10^5$ to $3 \times 10^6$ cells per milliliter.

5. The process of claim 2, wherein said malignant murine cells are clones of said T leukemic cells or T lymphoma cells.

6. The process of claim 5, wherein said clones of said T lymphoma cells are clones of LBRM-33 lymphoma murine T-cells.

7. The process of claim 5, or 6, wherein the initial T leukemic clone or T lymphoma clone cell concentration is in the range of about $6 \times 10^5$ to $3 \times 10^6$ cells per milliliter.

8. The process of claims 1, 2, 3, 5, or 6, wherein the T-cell mitogen in the culture medium is a compound selected from the group consisting of phytohemagglutinin, concanavalin A and pokeweed mitogen.

9. The process of claim 8, wherein the concentration of phytohemagglutinin mitogen is between 0.5 and 2.0% by volume.

10. The process of claim 8, wherein the concentration of concanavalin A mitogen is between 10 and 50 micrograms per milliliter.

11. The process of claim 8, wherein the culture medium further includes a phorbol ester derivative.

12. The process of claim 11, wherein the phorbol ester derivative includes phorbol myristate acetate.

13. The process of claim 12, wherein the phorbol myristate acetate is in a concentration of approximately 10 to 50 nanograms per milliliter.

14. The process of claim 8, wherein the culture medium further includes either Roswell Park Memorial Institute medium, Click's medium, or Dulbecco Modified Eagle Medium.

15. The process of claim 8, comprising recovering the IL-2 from the culture medium after approximately twenty-four to forty-eight hours of culturing.

16. The process of claim 1, 2, 3, 5, or 6, wherein the culture medium further contains a compound selected from a group consisting of Roswell Park Memorial Institute medium, Click's medium, or Dulbecco Modified Eagle Medium.

17. The process of claim 16, wherein the culture medium further contains one or more compounds selected from the group consisting of penicillin, streptomycin, glutamine, Hepes buffer, $NaHCO_3$, fetal calf serum and 2-mercaptoethanol.

18. A process for producing IL-2 from a murine malignant T-cell line, comprising cloning malignant murine T-cells, culturing the cloned malignant murine T-cells in a culture medium containing a T-cell mitogen, and recovering the IL-2 from the culture medium.

19. The process of claim 18, wherein said cloned malignant murine T-cells are cloned from T leukemic cells or lymphoma cells.

20. The process of claim 19, wherein said cloned T lymphoma cells are clones of LBRM-33 lymphoma murine T-cells.

21. The process of claim 18, 19 or 20 wherein the T-cell mitogen in the culture medium is a compound selected from the group consisting of phytohemagglutinin, concanavalin A, or pokeweed mitogen.

22. The process of claim 21, wherein the culture medium further includes a phorbol ester derivative.

23. The process of claim 22, wherein the phorbol ester derivative includes a phorbol myristate acetate.

24. The process of claims 18, 19, or 20, wherein the culture medium further includes either Roswell Park Memorial Institute medium, Click's medium or Dulbecco Modified Eagle medium.

25. The process of claims 18, 19 or 20, comprising recovering of the IL-2 from the culture medium after approximately sixteen to forty-eight hours of culturing.

* * * * *

UNITED STATES PATENT AND TRADEMARK OFFICE
CERTIFICATE OF CORRECTION

PATENT NO. : 4,411,992　　　　　　　　　　　　　　　　Page 1 of 2

DATED : October 25, 1983

INVENTOR(S) : Steven Gillis

It is certified that error appears in the above-identified patent and that said Letters Patent is hereby corrected as shown below:

| | |
|---|---|
| Column 1, line 34: | delete ")" 1st occurrence. |
| Column 1, line 39: | "culute" should be --culture--. |
| Column 2, line 28: | "above cited" should be --above-cited--. |
| Column 2, line 63: | "tomor" should be --tumor--. |
| Column 3, line 8: | insert "," (comma) after "Con A". |
| Column 3, line 44: | "millileter" should be --milliliter--. |
| Column 3, line 49: | insert "a" before "graph". |
| Column 3, line 51: | "IL2" should be --IL-2--. |
| Table 1, line 4: | "E1-4" should be --EL-4--. |
| Column 5, line 34: | "FIG." should be --FIGS.--. |
| Column 6, line 53: | "IL-2production" should be --IL-2 production--. |
| Column 7, line 17: | "aare" should be --are--. |
| Column 8, line 4: | insert "," (comma) after "Co.". |
| Column 8, line 16: | insert "," (comma) after "RBL-3". |
| Column 8, line 23: | insert "," (comma) after "Con A". |
| Column 8, line 35: | insert "," (comma) after "RBL-31C". |

UNITED STATES PATENT AND TRADEMARK OFFICE
CERTIFICATE OF CORRECTION

PATENT NO. : 4,411,992                    Page 2 of 2

DATED : October 25, 1983

INVENTOR(S) : Steven Gillis

It is certified that error appears in the above-identified patent and that said Letters Patent is hereby corrected as shown below:

Column 10, line 3: insert "," (comma) after "instance".
Column 10, line 6: "cultures" should be --cultured--.
Column 10, line 14: "," (comma) should be --.-- (period).
Column 10, line 33: "Il-2" should be --IL-2--.
Column 10, line 37: "chromotography" should be --chromatography--.
Column 10, line 41: "Il-2" should be --IL-2--.
Column 11, line 54: "." should be --:--.
Column 12, line 39: "was" should be --were--.
Column 12, line 66: "island" should be --Island--.
Column 13, line 10: "cluture" should be --culture--.
Column 13, line 23: insert "," (comma) after "i.e.,".

Signed and Sealed this

Twenty-eighth Day of August 1984

[SEAL]

Attest:

GERALD J. MOSSINGHOFF

Attesting Officer       Commissioner of Patents and Trademarks